US008623861B2

(12) United States Patent
Li

(10) Patent No.: US 8,623,861 B2
(45) Date of Patent: Jan. 7, 2014

(54) METHOD OF TREATING DEMYELINATION DISEASES

(76) Inventor: Xin-Min Li, Saskatoon (CA)

(*) Notice: Subject to any disclaimer, the term of this patent is extended or adjusted under 35 U.S.C. 154(b) by 594 days.

(21) Appl. No.: 12/513,197

(22) PCT Filed: Nov. 5, 2007

(86) PCT No.: PCT/CA2007/001978
§ 371 (c)(1),
(2), (4) Date: Jan. 25, 2010

(87) PCT Pub. No.: WO2008/052354
PCT Pub. Date: May 8, 2008

(65) Prior Publication Data
US 2010/0216771 A1    Aug. 26, 2010

Related U.S. Application Data

(60) Provisional application No. 60/864,223, filed on Nov. 3, 2006.

(51) Int. Cl.
*A61K 31/554* (2006.01)
*A01N 43/60* (2006.01)
*A61K 31/497* (2006.01)

(52) U.S. Cl.
USPC .......... 514/211.09; 514/211.15; 514/249; 514/252.12; 514/903

(58) Field of Classification Search
USPC .......... 514/211.09, 211.15, 249, 252.12, 903
See application file for complete search history.

(56) References Cited

U.S. PATENT DOCUMENTS

| | | | |
|---|---|---|---|
| 4,879,288 A | 11/1989 | Warawa et al. | |
| 7,563,785 B2 * | 7/2009 | Edgar et al. | 514/211.13 |
| 2004/0058909 A1 | 3/2004 | Goldstein | |
| 2004/0058910 A1 | 3/2004 | Brown et al. | |
| 2004/0220400 A1 | 11/2004 | Diller et al. | |
| 2004/0228914 A1 | 11/2004 | Brown | |
| 2005/0158383 A1 | 7/2005 | Boehm et al. | |
| 2006/0063927 A1 | 3/2006 | Etlin et al. | |
| 2006/0094705 A1 | 5/2006 | Edgar et al. | |
| 2006/0159768 A1 | 7/2006 | Brown | |
| 2006/0189594 A1 | 8/2006 | Puig et al. | |

OTHER PUBLICATIONS

Pithadia et al. "Guillain-Barre syndrome (GBS)". Pharmacological Reports, 2010, 62, 220-232.*
Berger Jr. "Progressive Multifocal Leukoencephalopathy and Newer Biological Agents". Drug Safety 2010; 33 (11): 969-983.*
Saidha et al. "New and emerging disease modifying therapies for multple sclerosis". Ann. N.Y. Acad. Sci., Jan. 2012; 1247: 117-37.*
de Groot et al. "In Vivo Induction of Glial Cell Proliferation and Axonal Outgrowth and Myelination by Brain-Derived Neurotrophic Factor" Molecular Endocrinology 20(11): 2987-2998 Nov. 1, 2006.*

Xu et al. "Quetiapine attenuates the immobilization stress-induced decrease of brain-derived neurotrophi factor expression in rat hippocampus". Neuroscience Letters 321 (2002) 65-68.*
Barnett et al. "The pathology of multiple sclerosis: a paradigm shift". Current Opinion in Neurology 2006, 19: 242-247.*
Horacek, et al., "Mechanisim of Action of Atypcial Antipsychotic Drugs and the Neurobiology of Schizophrenia", CNS Drugs, May 2006, 20, 389-409.
Xu, et al., "Quetiapine Attenuates the Immobilization Stress-induced Decrease of Brain Derived Neurotrophic Faction Expression in Rat Hippocampus", Neurosciences Letters, 2002, 321, 65-68.
De Groot, et al., "In Vivo Induction of Glial Cell Proliferation and Axonal Outgrowth and Myelinaiton by Brain Derived Neurotrophic Factor", Molecular Endocrinology, Aug. 2006, 20, 2987-2998.
Bai, O et al., "Protective effects of atypical antipsychotic drugs on PC12 cells after serum withdrawal" J Neurosci Res. 69(2); 278-283, 2002.
Farber, NB et al., "Olanzapine and fluperlapine mimic clozapine in preventing MK-801 neurotoxicity" Schizophr Res 21(1), 33-37, 1996.
Farber, NB et al., Antipsychotic drug block phencycliidne receptor-medicated neurotoxicity:, Biol Psychiatry 34(1-2), 119-121, 1993.
Fuijimura, M et al., "Effects of antipsychotic drugs on neurotoxicity, expression of fos-like protein and c-fos mRNA in the retrosplenial cortex after administration of dizocilipine", Eur J Pharmacol, 398(1), 1-10, 2000.
Hashimoto, K. et al., "Dizocilpine-induced neuropathological changes in rat retrosplenial cortex are reversed by subsequent clozapine treatment" Life Sci. 66 (12): 1017-1078,3. 2000.
He, J., et al. "The effects of chronic administration of quetiapine on the phencyclidine-induced reference memory impairment and decrease of Bcl-XL/Bax ratio in the posterior cingulate cortex in rats", Behav Brain Res. 168(2), 236-242, 2006.
He, J., et al. "Neuroportective effects of olanzapine on methamphetamine-induced neurotoxicity are associated with an inhibition of hyperthermia and prevention of Bcl-2 decrease in rats" Brain Res, 1018(2), 186-192, 2004.
He, J., et al. "Chronic adminstration of quetiapine alleviates the anixety-like behavioural changes induced by a neurotoxic regimen of dl-amphetamine in rats" Behav Brain Res. 160(1), 178-187, 2005.
Jarskog, LF et al., "Caspase-3 Activation in Rat Frontal Cortex Following Treatment with Typical and Atypical Antiphsychotics.", Neuropsychopharmacology. Apr. 12, 2006.
Luo, C. et al., "Post-stress changes in BDNF and Bcl-2 immunoreactivities in hippocampal neurons: effect of chronic administration of olonazpin" Brain Res. 1025(1-2); 194-202, 2004.
Martin, MV et al. "Low dose quetiapine reverses deficits in contextual and cued fear conditioning in rats with excitotoxin-induced hippocampal neuropathy", Pharmacol Biochem Behav. 82(2), 263-269, 2005.

(Continued)

*Primary Examiner* — Renee Claytor
(74) *Attorney, Agent, or Firm* — Bereskin & Parr LLP/S.E.N.C.R.L., s.r.l.; Patricia Folkins

(57) ABSTRACT

The present invention relates to a method of treating demyelination diseases, such as multiple sclerosis, comprising administration of an atypical antipsychotic drug, such as quetiapine or an analog thereof, to a subject in need thereof.

5 Claims, 10 Drawing Sheets

(56) References Cited

OTHER PUBLICATIONS

Parikh, V et al., "Nerve growth factor in never-medicated first episode psychotic and medicated chronic schizophrenic patients: possible implications for treatment outcome" Schizophrenia Res 60(2-3), 117-123, 2003.

Qing, H et al., "The ability of atypical antipsychotic drugs vs. haloperidol to protect PC12 cells against MPP+-induced apoptosis", Eur J Neurosci 17(8), 1563-1570, 2003.

Thanvi, BR et al., "Atypical antipsychotics in the treatment of affective symptoms: a review" Ann Clin Psychiatry. 16 (1), 3-13, 2004.

Wang, H., et al., "Olanzapine and queitapine protect PC12 cells from beta-amyloid peptide (25-35)-induced oxidative stress and the ensuing apoptosis" J Neurosci Res. 81(4), 572-580, 2005.

Wei, Z, et al., "Olanzapine protects PC12 cells from oxidatives stress induced by hydrogen peroxide", J Neurosci Res, 73(3), 364-368, 2003.

English Translation of Examination Report for Chinese Patent Application No. 2007 80049155.2, Jun. 1, 2011.

Chan, et al., "Neurotrophins Are Key Mediators of the Myelination Program in the Peripheral Nervous System", PNAS, 2001, 98, 14661-14668.

Tolwani, et al., "BDNF Overexpression Produces a Long-term Increase in Myelin Formation in the Peripheral Nervous System", J. Neuroscience Research, 2004, 77, 662-669.

Stadelmann, et al., "BDNF and gp145trkB in Multiple Sclerosis Brain Lesions: Neuroprotective Interactions Between Immune and Neuronal Cells", Brain, 2002, 125, 75-85.

Karoutzou, et al., "The Myelin-pathegonesis Puzzle in Schizophrenia: A Literature Review", Molecular Psychology, Oct. 2007, 1-16.

Davids, et al., "Antipsychotic Treatment of Psychosis Associated with Multiple Sclerosis", Progress in Neuro-Psychopharmacology & Biological Psychiatry, 2004, 28, 743-744.

Tkachev, et al., "Oligodendrocyte Dysfunction in Schizophrenia and Bipolar Disorder", The Lancet, 2003, 362, 798-805.

* cited by examiner

Fig. 1.A
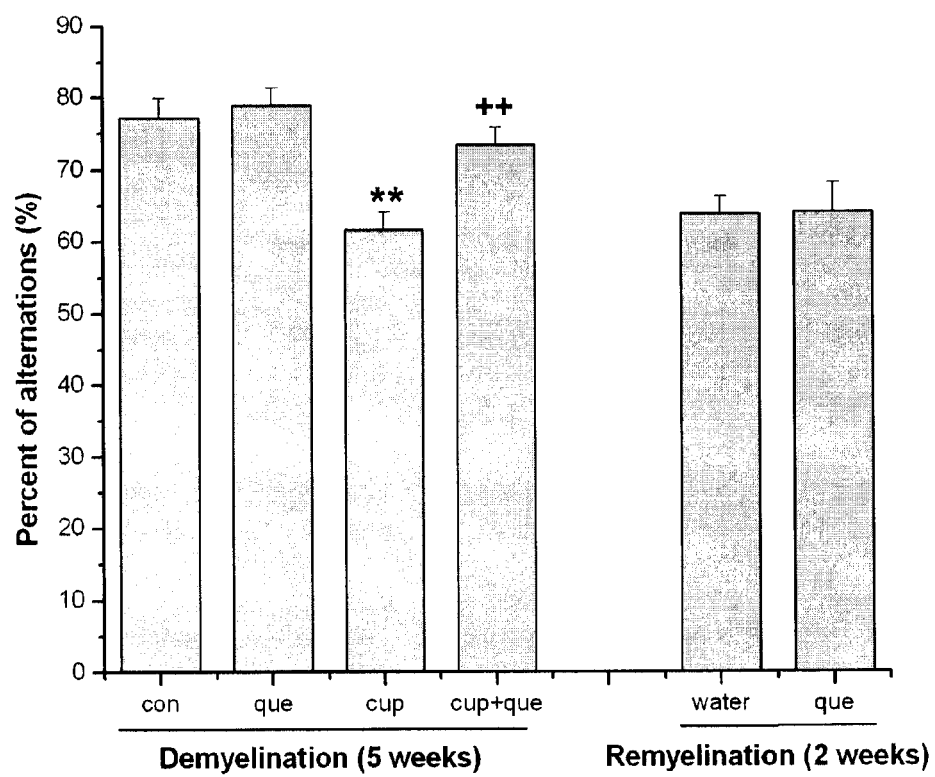

Fig. 1.B
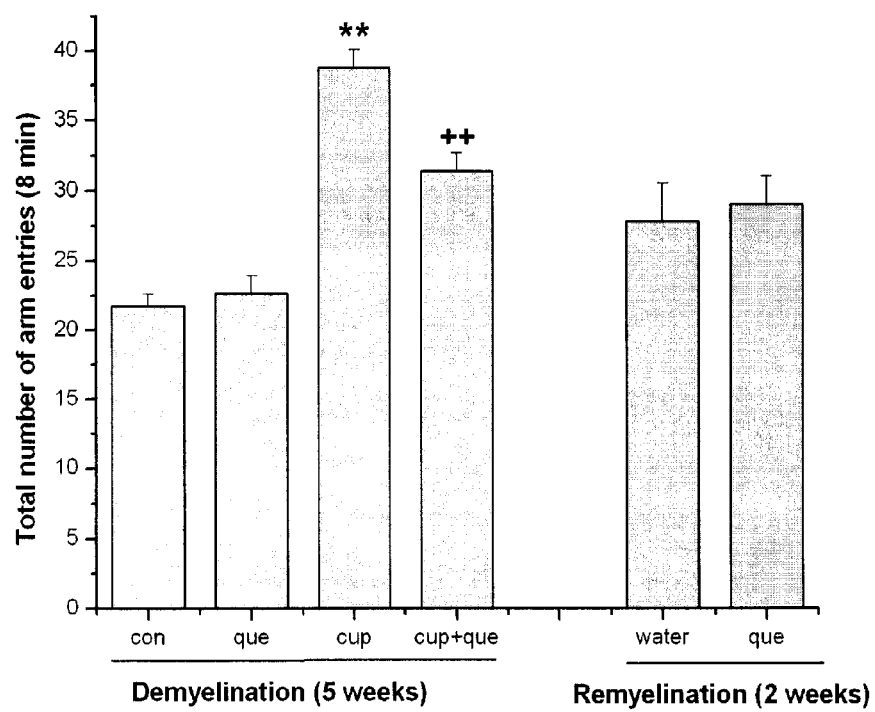

Fig. 2.A-F
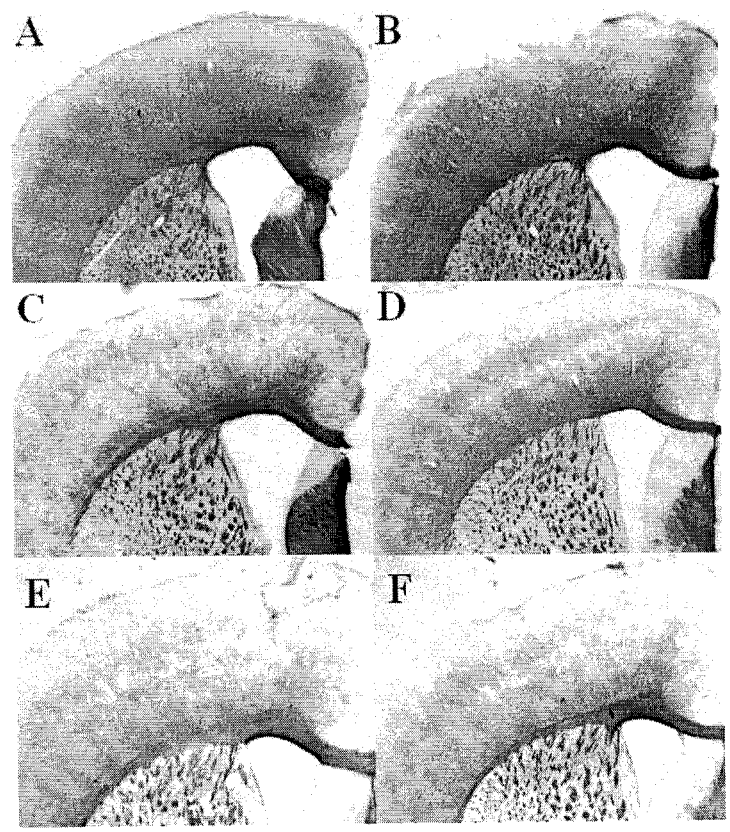

Fig. 2.G-H
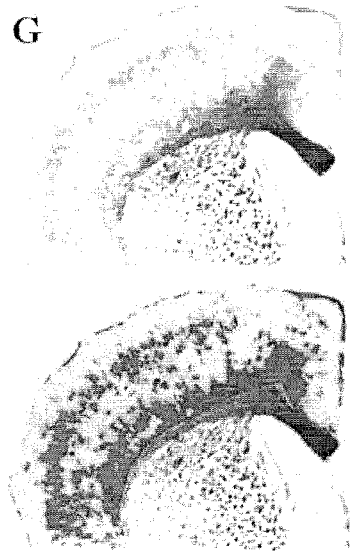
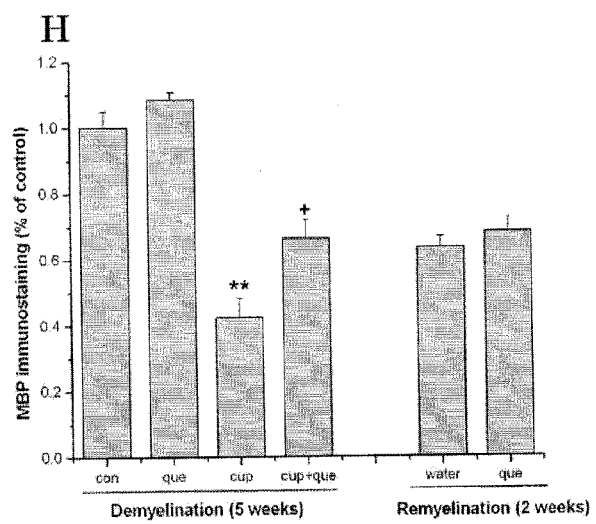

Fig. 3.A-F
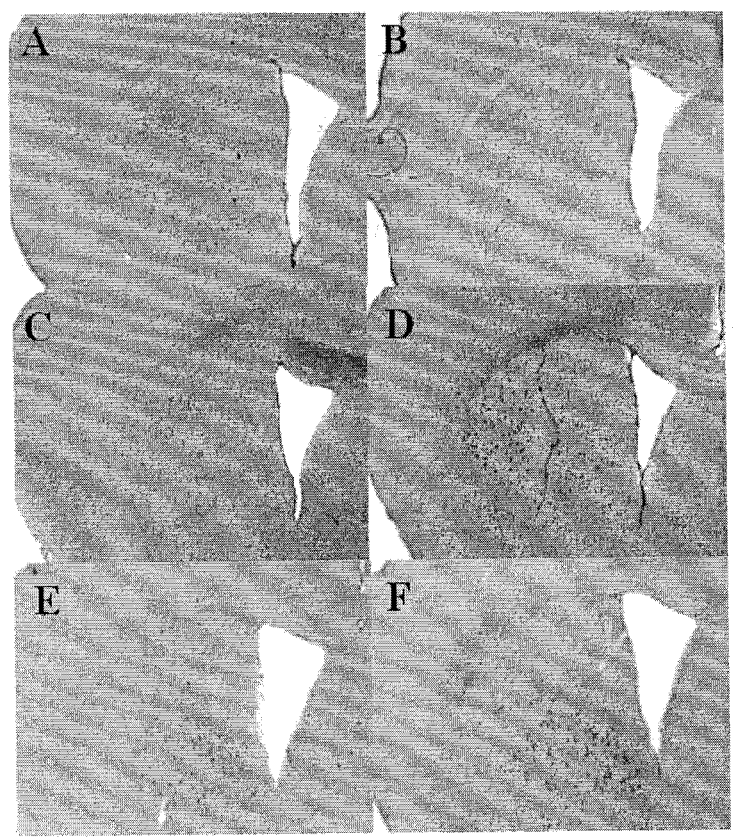

Fig. 4.A-E
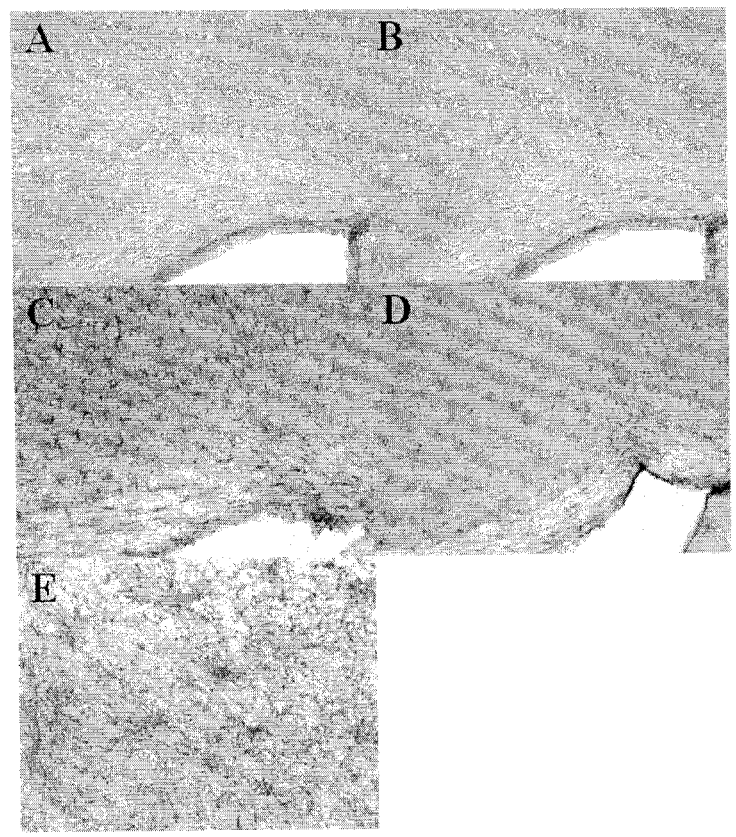

Fig. 4.F-G.
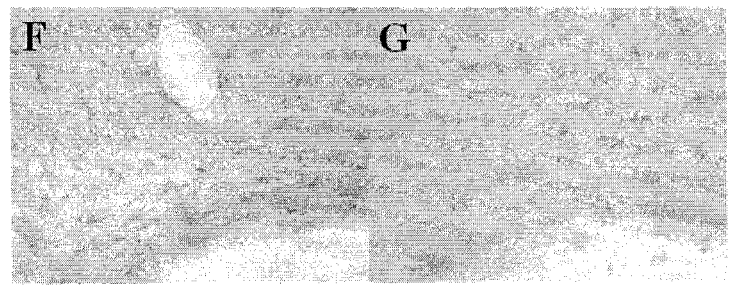

Fig. 4.H
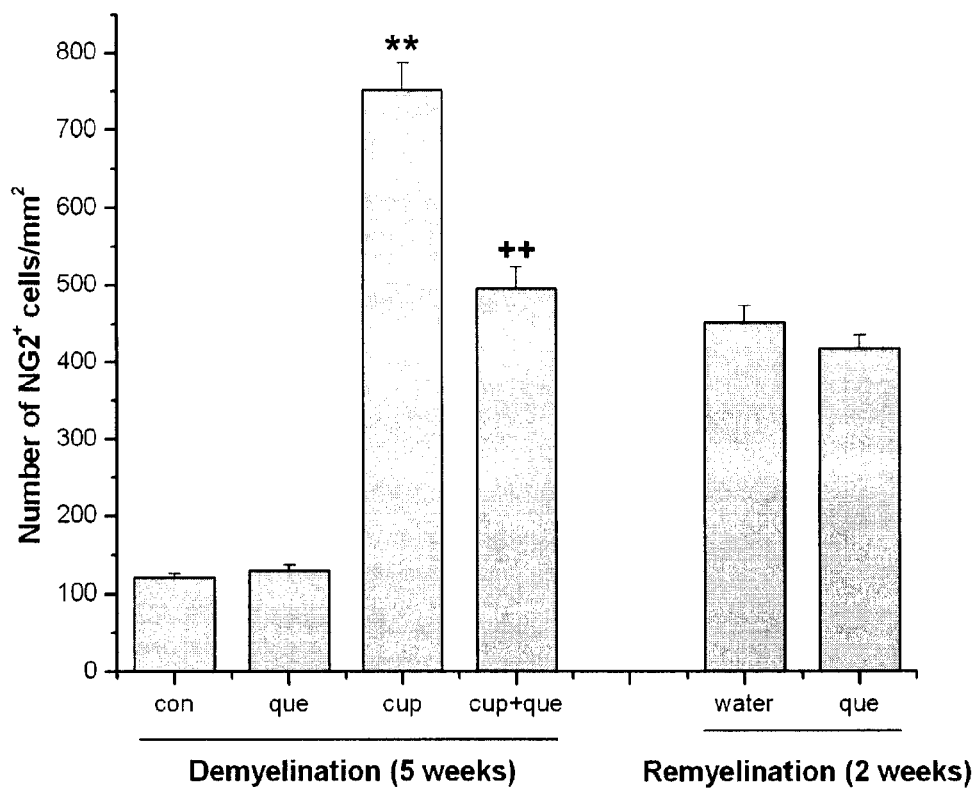

Fig. 5.A-F
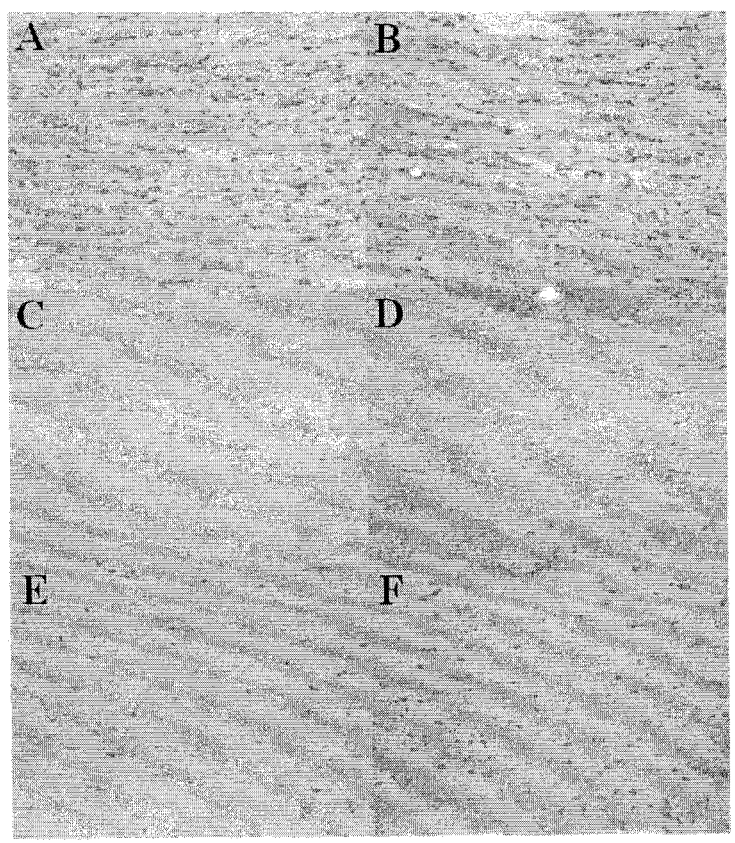

Fig.5.G
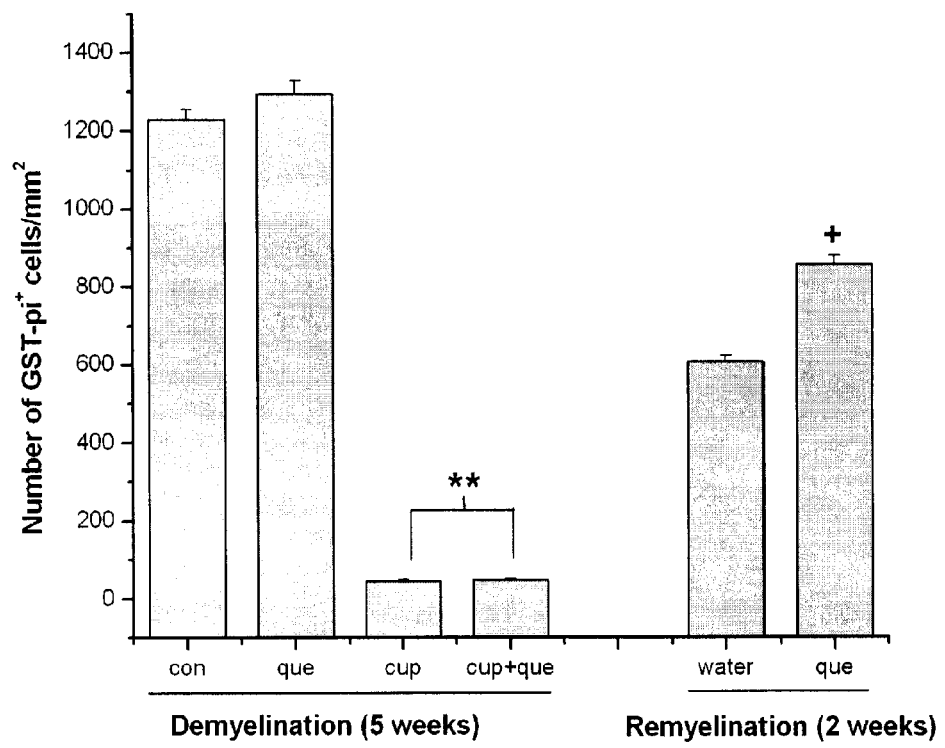

METHOD OF TREATING DEMYELINATION DISEASES

This application is a National Stage of International Application No. PCT/CA2007/001978, filed Nov. 5, 2007, which claims the benefit of Provisional Application No. 60/864,223, filed Nov. 3, 2006, the contents of which are herein incorporated by reference.

FIELD OF THE INVENTION

The present invention relates a method of treating demyelination diseases. In particular the method involves the administration of atypical antipsychotics, such as quetiapine or a structural analog thereof, to treat demyelination diseases, for example multiple sclerosis, in a subject in need thereof.

BACKGROUND OF THE INVENTION

Myelin sheaths, which cover many nerve fibers, are composed of lipoprotein layers formed in early life. Myelin formed by the oligodendroglia in the CNS differs chemically and immunologically from that formed by the Schwann cells peripherally, but both types have the same function: to promote transmission of a neural impulse along an axon.

Many congenital metabolic disorders (eg, phenylketonuria and other aminoacidurias; Tay-Sachs, Niemann-Pick, and Gaucher's diseases; Hurler's syndrome; Krabbe's disease and other leukodystrophies) affect the developing myelin sheath, mainly in the CNS. Unless the biochemical defect can be corrected or compensated for, permanent, often widespread, neurologic deficits result.

Demyelination in later life is a feature of many neurologic disorders; it can result from damage to nerves or myelin due to local injury, ischemia, toxic agents, or metabolic disorders. Extensive myelin loss is usually followed by axonal degeneration and often by cell body degeneration, both of which may be irreversible. However, remyelination occurs in many instances, and repair, regeneration, and complete recovery of neural function can be rapid. Recovery often occurs after the segmental demyelination that characterizes many peripheral neuropathies; this process may account for the exacerbations and remissions of multiple sclerosis (MS). Central demyelination (ie, of the spinal cord, brain, or optic nerves) is the predominant finding in the primary demyelinating diseases, whose etiology is unknown. The most well known is MS. Other diseases include, for example, acute disseminated encephalomyelitis (postinfectious encephalomyelitis), adrenoleukodystrophy, adrenomyeloneuropathy, Leber's hereditary optic atrophy and related mitochondrial disorders and human T-cell lymphotropic virus (HTLV) infection-associated myelopathy.

Multiple sclerosis (MS) is a chronic inflammatory disease of the central nervous system (CNS). In pathology, the disease is characterized as scattered demyelination lesions, axonal loss and damage in both the brain and spinal cord (Lassmann, 2005), which results in a multiplicity of neurological deficits. Current therapies for managing patients with MS primarily target the inflammatory aspect of the disease (Zamvil and Steinman, 2003) and are only partly effective and limited by side effects. Recent studies suggest that glutamate-mediated cytotoxicity (excitotoxicity) (Stover et al., 1997; Barkhatova et al., 1998; Smith et al., 1999; Pitt, 2000), oxidative stress (Gilgum-Sherki et al., 2004) and mitochondrial damage (Andrews et al., 2005), may play vital roles in the pathogenesis of MS.

Remyelination is generally accepted as a regular event in MS lesions (Prineas et al., 1993; Raine et al., 1993); however, it is insufficient for myelin repair and axons remain demyelinated in MS patients (Prineas et al., 1993; Lovas et al., 2000). Possible explanations for this include failure of recruitment or survival of oligodendrocyte progenitor cells (OPCs), disturbance of differentiation/maturation of OPCs, and loss of capability of myelin forming (Wolswijk et al., 1998; Chang et al., 2003). Therefore, effective interventions for MS should not only prevent disease progression, but also promote remyelination.

Quetiapine is an atypical antipsychotic which has good efficacy and tolerability and which is useful in the treatment of schizophrenia. The use of quetiapine for the treatment of Parkinson's disease (Goldstein, 2004) and substance abuse (Brown, 2004) has also been proposed.

Atypical antipsychotic drugs (APDs), such as clozapine and quetiapine, have been widely used for treating a range of severe psychiatric disorders (Thanvi et al., 2004; Gao et al., 2005) and mental symptoms in neurological diseases (Baum et al., 2003; Bosboom et al., 2004; Altschuler et al., 2005; Carson et al., 2006). Neuroprotective effects of APDs have recently been highlighted in both in vitro and in vivo studies as new features of their therapies. In 1993, Farber and colleagues reported that the neurotoxicity produced by dizocilpine, an N-methyl-D-aspartic acid (NMDA) receptor antagonist, in the rat retrosplenial cortex could be significantly decreased by clozapine pre-treatment (Farber et al., 1993). A subsequent study showed that olanzapine had the same effect in preventing MK-801-induced neurotoxicity (Farber et al., 1996). Other groups also reported that pre-treatment with clozapine or olanzapine blocked the neuronal vacuolization and significantly attenuated the expression of Fos-like protein in the rat retrosplenial cortex induced by dizocilpine (Fujimura et al., 2000; Hashimoto et al., 2000).

It has been demonstrated that quetiapine and olanzapine could attenuate the immobilization stress-induced decrease in the expression of BDNF in rat hippocampus (Xu et al., 2002; Luo et al., 2004), and modulate the short- and long-term behavioral consequences of chronic administration of dl-amphetamine in rats (He et al., 2005). In vitro studies also supported that the APDs clozapine, olanzapine, quetiapine, and risperidone can reduce the PC 12 cell death caused by serum withdrawal or the addition of hydrogen peroxide, β-amyloid peptide, or 1-methyl-4-phenylpyridinium (MPP+). These protective effects may be related to the regulation of expression of the low affinity NGF receptor p75 and SOD1 in PC2 cells by the drugs (Bai et al., 2002; Wei et al., 2003, Qing et al., 2003). Results from a clinical trial indicated that atypical drug treatment markedly increased the levels of plasma NGF in schizophrenia patients compared with never-treated patients or the patients treated with typical agents (Parikh et al., 2003).

SUMMARY OF THE INVENTION

In the present application, using an established de- and re-myelination model, it has been shown that quetiapine, an atypical antipsychotic drug (APD) decreases the demyelination induced by cuprizone and promotes mature oligodendrocyte resettlement in demyelinated areas during the remyelination process in mouse brain. Specifically, in the present study, it was demonstrated that: (1) co-administration of quetiapine attenuates cuprizone-induced demyelination; (2) feeding with cuprizone causes spatial memory impairment in mice that is reversed by quetiapine treatment; (3) quetiapine alleviates the activation and accumulation of oligodendrocyte progenitors responding to demyelination; (4) quetiapine does not alter the depletion of mature oligodendrocytes in the demyelinated area; and (5) during the remyelination process, quetiapine treatment promotes repopulation of mature oligodendrocytes in lesions.

Accordingly the present invention includes a method of treating a demyelination disease comprising administering to a subject in need thereof, an effective amount of a compound selected from quetiapine and analogs of quetiapine, and pharmaceutically acceptable salts, solvates and prodrugs thereof, said compound being effective for the attenuation of demyelination in said subject.

The present invention also includes a use of a compound selected from quetiapine and analogs of quetiapine, and pharmaceutically acceptable salts, solvates and prodrugs thereof, to treat a demyelination disease, said compound being effective for the attenuation of demyelination in said subject. Further, the present invention includes a use of a compound selected from quetiapine and analogs of quetiapine, and pharmaceutically acceptable salts, solvates and prodrugs thereof, to prepare a medicament to treat a demyelination disease, said drug being effective for the attenuation of demyelination in said subject.

In an embodiment of the invention, the demyelination disease is multiple sclerosis.

Quetiapine attenuates demyelination and reverses memory impairment induced by cuprizone. During the remyelination, quetiapine promotes mature oligodendrocyte repopulation in demyelinated lesions. This is the first time the effects of quetiapine on demyelination and remyelination have been looked at. Due to the complicated pathogenesis of MS, current immunomodulation treatments have limited effects on preventing demyelination and promoting remyelination. By taking advantage of the neuroprotection, the effects on oligodendrocyte regulation, and cognitive dysfunction management, atypical antipsychotic drugs, such as quetiapine, are candidates for treating patients with demyelination disorders, such as, multiple sclerosis.

This Summary of Invention lists several embodiments of the invention, and in many cases lists variations and permutations of these embodiments. The Summary is merely exemplary of the numerous and varied embodiments. Mention of one or more specific features of a given embodiment is likewise exemplary. Such embodiment can typically exist with or without the feature(s) mentioned; likewise, those features can be applied to other embodiments of the invention, whether listed in this Summary or not. To avoid excessive repetition, this Summary does not list or suggest all possible combinations of such features.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the effects of quetiapine on cuprizone-induced impairment of spontaneous alternation performance (A) and total number of arm entries (B) in an 8-minute Y-maze test. Mice were fed with 0.2% cuprizone for 5 weeks with vehicle (water) (cup) or quetiapine treatment (cup+que); age-matched mice were fed with normal chow (con) and quetiapine treatment alone (que). Y-maze test was performed at the end of the treatment. For remyelination, cuprizone was given for 6 weeks, and then backed to a normal diet with quetiapine (que) (10 mg/kg/day in water) or vehicle (water) treatment for 2 weeks. Data are expressed as the mean±S.E.M. 6-8 mice of each group were examined. **P<0.01 vs. control, ++P<0.01 vs. cuprizone alone (Tukey's test).

FIG. 2 shows demyelination and remyelination in the corpus callosum of mice. MBP immunostaining shows demyelination in the corpus callosum after 5 weeks of cuprizone treatment (C). Quetiapine treatment attenuates the demyelination significantly (D). Control (A) and quetiapine alone (B) show no difference on myelination. To evaluate the rate of remyelination, after the 5-week cuprizone feeding, mice were fed with normal chow for another 2 weeks during the remyelination process. The demyelination lesions rapidly recovered. Quetiapine (F) had no difference with vehicle (water, E) on myelin repair (MBP staining, magnification, ×4). The area of MBP staining was scored (G). The results represent the mean of the percent of MBP staining area of control (Mean+S.E.M.). 6-8 mice of each group were examined. **P<0.01 vs. control, ++P<0.01 vs. cuprizone alone (Tukey's test).

FIG. 3 shows that quetiapine administration protects against the demyelination caused by cuprizone. Mice were fed with 0.2% cuprizone for 5 weeks with vehicle (water) (C) or quetiapine treatment (D); age-matched mice were fed with normal chow (A) and quetiapine treatment alone (B). Coronal brain sections at the level of the corpus callosum were stained with LFB-PAS. To evaluate the rate of remyelination, after a 5-week cuprizone feeding, mice were fed with normal food for another 2 weeks. Representative brain coronal sections stained with LFB/PAS (magnification, ×4) are shown of vehicle (water, E) and quetiapine-treated mice (F) at 2 weeks of feeding with normal food after 6 weeks of cuprizone feeding.

FIG. 4 shows that quetiapine decreases the accumulation of OPCs during demyelination after cuprizone treatment. A: Frozen coronal brain sections were stained with NG2 antibody. A higher accumulation of OPCs was observed after 5 weeks of cuprizone treatment (C) compared to the cup+que group (D). Few NG2+ cells were observed in the control (A) and quetiapine alone (B) groups. Cuprizone treatment stimulates NG2+ cells differentiated into star-like immature oligodendrocytes (E). During remyelination, accumulation of OPCs is reduced, no difference was observed between water (F) and quetiapine treatment (G). The data represents the mean number of NG2+ cells in the corpus callosum (Mean±S.E.M.). 6-8 mice of each group were examined. **P<0.01 vs. control, ++P<0.01 vs. cuprizone alone (Tukey's test). Magnification, ×10 for A, B, C and D; ×40 for E; ×20 for F and G.

FIG. 5 shows the effect of quetiapine on the number of mature oligodendrocytes during cuprizone-induced demyelination. The mature oligodendrocytes in the corpus callosum were analyzed by staining with anti-GST-pi antibody. Cuprizone treatment dramatically decreases GST-pi+ cells in the corpus callosum (C); quetiapine did not seem protective for the depletion of mature oligodendrocytes (D). Compared to control (A), quetiapine alone treatment (B) had no difference. Interestingly, compared to water (E), quetiapine (F) increased the number of GST-pi+ cells in the remyelination process. The results represent the mean number of GST-pi-positive cells per square millimeter in the corpus callosum (G)**$p<0.01$ vs. control; +$p<0.05$ vs. water. Student's t test. Magnification, ×20.

DETAILED DESCRIPTION OF THE INVENTION

Quetiapine is an atypical antipsychotic drug widely used in treating neuropsychiatric disorders. Previous studies have demonstrated that quetiapine provides neuroprotective effects, following various insults to animals or cells in cultures. In vitro data indicates that quetiapine selectively promotes neural stem cell differentiation into oligodendrocyte lineage and facilitates myelin forming. To examine the effects of quetiapine on demyelination and remyelination in vivo, young C57BL/6 mice were exposed to cuprizone intoxication (0.2% w/w in chow) for 5 weeks with continuous treatment of quetiapine (10 mg/kg/day, p.o.) or vehicle (water). Compared to vehicle treatment, demyelination in the brain was significantly decreased in quetiapine-treated mice. This reduction of demyelination is correlated to decrease in oligodendrocyte progenitor cell accumulation. Quetiapine also improves the working memory impairment caused by cuprizone treatment in mice. When cuprizone is removed from the diet, remyelination occurs spontaneously. During the remyelination process, quetiapine treatment dramatically increases mature oligodendrocyte resettlement in demyelinated areas; which is possibly facilitated by oligodendrocyte progenitor proliferation and differentiation. This data indicates that quetiapine will have beneficial effects on both de- and re-myelination, meaning that quetiapine and its analogs will be a candidate for treating demyelinating diseases like multiple sclerosis (MS).

Accordingly the present invention includes a method of treating a demyelination disease comprising administering to a subject in need thereof, an effective amount of a compound selected from quetiapine and analogs of quetiapine, and pharmaceutically acceptable salts, solvates and prodrugs thereof, said compound being effective for the attenuation of demyelination in said subject.

The present invention also includes a use of a compound selected from quetiapine and analogs of quetiapine, and pharmaceutically acceptable salts, solvates and prodrugs thereof, to treat a demyelination disease, said compound being effective for the attenuation of demyelination in said subject. Further, the present invention includes a use of a compound selected from quetiapine and analogs of quetiapine, and pharmaceutically acceptable salts, solvates and prodrugs thereof, to prepare a medicament to treat a demyelination disease, said drug being effective for the attenuation of demyelination in said subject.

The compound is one that is effective for the attenuation of demyelination in a subject. By "attenuation of demylination" it is meant that the amount of demyelination in the subject as a result of the disease or as a symptom of the disease is reduced when compared to otherwise same conditions and/or the amount of remyelination in the subject is increased when compared to otherwise same conditions. By "reduced" it is meant any measurable or detectable reduction in the amount of demyelination or in any symptom of the demyelination disease that is attributable to demyelination. Likewise, the term "increased" means any measurable or detectable increase in the amount of remyelination which will also manifest as a reduction in any symptom of the demyelination disease that is attributable to demyelination. In an embodiment of the invention, attenuation of demyelination in a subject is as compared to a control. Symptoms attributable to demyelination will vary depending on the disease but may include, for example but not limited to, neurological deficits, such as cognitive impairment (including memory, attention, conceptualization and problem-solving skills) and information processing; paresthesias in one or more extremities, in the trunk, or on one side of the face; weakness or clumsiness of a leg or hand; or visual disturbances, eg, partial blindness and pain in one eye (retrobulbar optic neuritis), dimness of vision, or scotomas.

The ability of a compound to attenuate demyelination may be detected or measured using assays known in the art, for example, the cuprizone induced demyelination model described herein.

Quetiapine is 11-(4-[2-(2-hydroxyethoxy)ethyl]-1-piperazinyldibenzo[b,f][1,4]-thiazepine, also known as Seroquel™, and has the following structure:

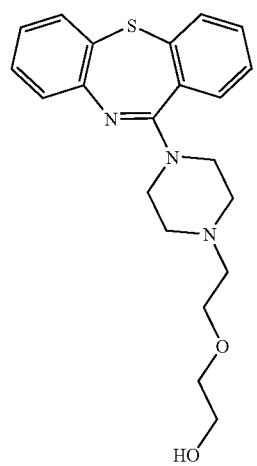 [SMILES: OCCOCCN1CCN(C2=Nc3ccccc3Sc3ccccc32)CC1]

This compound, pharmaceutically acceptable salts thereof and its use in treating schizophrenia are described in U.S. Pat. No. 4,879,288 (Warawa et al.). Novel polymorphs of quetiapine are described in U.S. Patent Application Publication No. 20040242562 (Parthasaradhi, et al.). The present invention extends to methods and uses of all forms of quetiapine, including amorphous and crystalline forms.

In an embodiment of the invention the compound is selected from quetiapine and pharmaceutically acceptable salts, solvates and prodrugs thereof, suitably a pharmaceutically acceptable salt thereof. In another embodiment of the invention, the compound is selected from an analog of quetiapine and pharmaceutically acceptable salts, solvates and prodrugs thereof, suitably a pharmaceutically acceptable salt thereof. Analogs of quetiapine are, for example, those described in U.S. Patent Application Publication No. 20060094705 (Edgar, et al.). Analogs of quetiapine also include metabolites of quetiapine, including the corresponding N-de-alkylated analog, the corresponding sulfoxide and sulfone analogs and corresponding phenolated analogs.

In an embodiment of the invention, the analogs of quitapine are selected from a compound of Formula I, and pharmaceutically acceptable salts, solvates and prodrugs thereof:

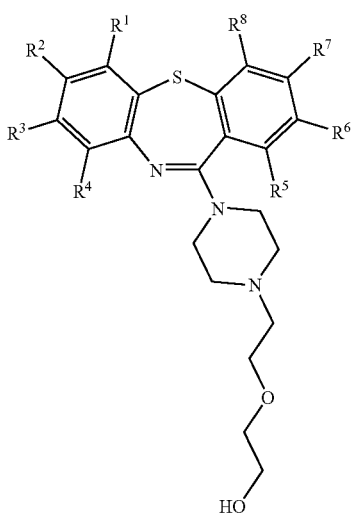

(I)

wherein one to four, suitably one to three of $R^1$, $R^2$, $R^3$, $R^4$, $R^5$, $R^6$, $R^7$ and $R^8$ are independently selected from Br, Cl, I, F, OH, $OCH_3$, $CF_3$, $OCF_3CH_3$, $CH_2CH_3$, $CH_2CH_2CH_3$, $CH_2(CH_3)_2$, $CH_2CH_2CH_2CH_3$, $CH_2CH_2(CH_3)_2$ and $C(CH_3)_3$.

In an embodiment of the invention, the demyelination disease is any disease or condition that results in damage to the protective covering (myelin sheath) that surrounds nerves in the brain and spinal cord. In a further embodiment of the invention, the demyelination disease is selected from multiple sclerosis, transverse myelitis, Guillain Barré syndrome, progressive multifocal leukoencephalopathy, transverse myelitis. phenylketonuria and other aminoacidurias, Tay-Sachs disease, Niemann-Pick disease, Gaucher's diseases, Hurler's syndrome, Krabbe's disease and other leukodystrophies, acute disseminated encephalomyelitis (postinfectious encephalomyelitis, adrenoleukodystrophy, adrenomyeloneuropathy, optic neuritis. Devic disease (neuromyelitis optica), Leber's hereditary optic atrophy and related mitochondrial disorders and HTLV-associated myelopathy or the demyelination disease is a result of local injury, ischemia, toxic agents, or metabolic disorders. In a further embodiment of the invention, the demyelination disease is multiple sclerosis.

The term "compounds of the invention" as used herein refers to a compound selected from quetiapine and an analog of quetiapine, and pharmaceutically acceptable salts, solvates and prodrugs thereof.

As used herein, and as well understood in the art, "treating" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder, means that the extent and/or undesirable clinical manifestations of a disorder or a disease state are lessened and/or time course of the progression is slowed or lengthened, as compared to not treating the disorder.

The term "pharmaceutically acceptable" means compatible with the treatment of animals, in particular, humans.

The term "pharmaceutically acceptable salt" means an acid or base addition salt which is suitable for or compatible with the treatment of patients.

The term "pharmaceutically acceptable acid addition salt" as used herein means any non-toxic organic or inorganic salt of any base compound of the invention. Basic compounds that may form an acid addition salt include those having a basic nitrogen. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds, for laboratory use, or for subsequent conversion to a pharmaceutically acceptable acid addition salt. In an embodiment of the invention, the pharmaceutically acceptable salt is a chloride, maleate, fumarate, citrate, phosphate, methane sulphonate or sulfate salt. In another embodiment of the invention, the pharmaceutically acceptable salt is a fumarate salt, for example a hemi-fumarate salt.

The term "pharmaceutically acceptable basic addition salt" as used herein means any non-toxic organic or inorganic base addition salt of any acid compound of the invention. Acidic compounds that may form a basic addition salt include, for example, those having a acidic hydrogen, for example, C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the compounds of the invention, for laboratory use, or for subsequent conversion to a pharmaceutically acceptable acid addition salt.

The formation of a desired compound salt is achieved using standard techniques. For example, the neutral compound is treated with an acid in a suitable solvent and the formed salt is isolated by filtration, extraction, recrystallization or any other suitable method.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the invention will vary depending on the identity of the compound and the solvate. In general, solvates are formed by dissolving the compound in the appropriate solvent and isolating the solvate by cooling or using an antisolvent. The solvate is typically dried or azeotroped under ambient conditions.

The methods of the present invention may also be carried out using prodrugs of quetiapine. Prodrugs are derivatives of quetiapine or quetiapine analogs, designed to undergo either a chemical or biochemical transformation in the subject to release the active compound. Prodrugs of quetiapine or quetiapine analogs may be, for example, conventional esters formed with available hydroxy groups. For example, an available hydroxy group may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters.

Methods of preparing quetiapine are reported in U.S. Pat. No. 4,879,288 (Warawa et al.), U.S. Patent Application Publication No. 20040220400 (Diller et al.), U.S. Patent Application Publication No. 20060063927 (Etlin et al.) and U.S. Patent Application Publication No. 20060189594 (Puig et al.).

The term "subject" as used herein includes all members of the animal kingdom including human. The subject is suitably a human.

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. For example, in the context of treating a demyelination disease, for example, it is an amount of the compound sufficient to achieve such an treatment as compared to the response obtained without administration of the compound. In the context of disease, therapeutically effective amounts of the compounds of the present invention are used to treat, modulate, attenuate, reverse, or effect a demyelination disease in a mammal. An "effective amount" is intended to mean that amount of a compound that is sufficient to treat, prevent or inhibit a demyelination disease. In some suitable embodiments, the amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces a demyelination disease in a subject as compared to a control. As defined herein, a therapeutically effective amount of a compound of the present invention may be readily determined by one of ordinary skill by routine methods known in the art.

The term "prevention" or "prophylaxis", or synonym thereto, as used herein refers to a reduction in the risk or probability of a patient becoming afflicted with a demyelination disease or manifesting a symptom associated with a demyelination disease.

The compounds of the invention may be used in the form of the free base, in the form of salts, solvates and/or prodrugs. All forms are within the scope of the invention. Suitably the compound is used in the form of a free base or a pharmaceutically acceptable salt.

In accordance with the methods of the invention, the compound of the invention, and/or salts, solvates and/or prodrugs thereof, may be administered to a patient in a variety of forms depending on the selected route of administration, as will be understood by those skilled in the art. A compound of the invention, and/or salts, solvates and/or prodrugs thereof, may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention, and/or salts, solvates and/or prodrugs thereof, may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like.

A compound of the invention, and/or salts, solvates and/or prodrugs thereof, may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

A compound of the invention, and/or salts, solvates and/or prodrugs thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of the invention, and/or salts, solvates and/or prodrugs thereof, may also be delivered by the use of monoclonal antibodies as individual carriers to which the compound molecules are coupled. A compound of the invention, and/or salts, solvates and/or prodrugs thereof, may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, a compound of the invention, and/or salts, solvates and/or prodrugs thereof, may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Formulations comprising quetiapine are known in the art (see for example, U.S. Patent Application Publications Nos. 20040228914, 20050158383 and 20060159768).

Compounds of the invention, and/or salts, solvates and/or prodrugs thereof, may be used alone or in combination with other known agents useful for treating or preventing demyelination diseases.

When used in combination with other agents useful in treating demyelination diseases, compounds of the invention, and/or salts, solvates and/or prodrugs thereof, is suitably administered contemporaneously with those agents. As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

Compounds of the invention, and/or salts, solvates and/or prodrugs thereof, may be administered to an animal alone or also in combination with pharmaceutically acceptable carriers, as noted above, the proportion of which is determined by the solubility and chemical nature of the compound, chosen route of administration and standard pharmaceutical practice.

The dosage of compounds of the invention, and/or salts, solvates and/or prodrugs thereof, can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. Compounds of the invention, and/or salts, solvates and/or prodrugs thereof, may be administered initially in a suitable dosage that may be adjusted as required, depending on the clinical response. As a representative example, oral dosages of compounds of the invention, and/or salts, solvates and/or prodrugs thereof, will range between about 1 mg per day to about 400 mg per day for an adult, suitably about 1 mg per day to about 200 mg per day, more suitably about 1 mg per day to about 20 mg per day. When formulated for oral administration, the compounds are suitably in the form of tablets containing 0.25, 0.5, 0.75, 1.0, 5.0, 10.0, 20.0, 25.0, 30.0, 40.0, 50.0, 60.0, 70.0 75.0, 80.0, 90.0, 100.0 150, 200, 250, 300, 350 or 400 mg of active ingredient per tablet. Suitably, for oral administration, the compounds are suitably in the form of tablets containing 0.25, 0.5, 0.75, 1.0, 5.0 or 10.0, mg of active ingredient per tablet. Compounds of the invention, and/or salts, solvates and/or prodrugs thereof, may be administered in a single daily dose or the total daily dose may be divided into two, three of four daily doses. If the compound of the invention, and/or salts, solvates and/or prodrugs thereof, are to be administered transdermally, using, for example, those forms of transdermal skin patches that are well known to those skilled in the art, the dosage administration will be continuous rather than intermittent throughout the dosage range.

In an embodiment of the invention, the compound of the invention, and/or salts, solvates and/or prodrugs thereof, is administered or used long term or chronically. The term "long term" and "chronic" or use or administration as used herein means that the compound of the invention, and/or a pharmaceutically acceptable salt, solvate and prodrug thereof, is administered to a subject on a continuous regular, long-term therapeutic basis. For example, the compound of the invention, and/or a pharmaceutically acceptable salt, solvate and prodrug thereof, may be administered to a subject without substantial interruption, such as, for example, daily, for a time period of at least several weeks or months to several years, for the purpose of treating the demyelination disease in a subject needing treatment. In an embodiment of the invention, the compound of the invention, and/or a pharmaceutically acceptable salt, solvate and prodrug thereof, is administered to a subject for at least about 2 months. In a further embodiment of the invention, the compound of the invention, and/or a pharmaceutically acceptable salt, solvate and prodrug thereof, is administered to a subject on an indefinite basis, for example for the rest of the subject's life, or until such administration does not have a beneficial effect or treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

EXAMPLES

Materials and Methods
Animals
C57BL/6 mice (8 weeks old, 20-25 g) were obtained from Charles River Canada (Montreal, QC, Canada) and housed in the University of Saskatchewan animal facility. All procedures were performed in accordance with the guidelines set by the Canadian Council on Animal Care (CCAC) and approved by the University Committee on Animal Care and Supply (UCACS), University of Saskatchewan.

Cuprizone-induced Demyelination/Remyelination and Administration of Quetiapine

To test whether quetiapine can protect mouse brain from cuprizone-induced demyelination, 8-week old mice were fed a diet of milled LabDiet® rodent chow (PMI nutrition international LLC, Brentwood, Mo., USA) containing 0.2% cuprizone for 5 weeks (w/w) (Sigma-Aldrich, St. Louis, Mo., USA) as previously described (Morell et al., 1998). Animals showed no severe side effects of this treatment. The study included the following 4 groups (6-8 animals/group): group 1: control, fed with regular chow (con); group 2: pre-administrated with quetiapine (10 mg/kg/day in drinking water) for 1 week, then followed by 5 weeks of quetiapine administration with normal diet (que); group 3: fed for 5 weeks on a cuprizone-containing diet (cup) with regular tap water for drinking; group 4: pre-administrated with quetiapine (10 mg/kg/day in drinking water) for 1 week, then followed by 5 weeks of quetiapine treatment with cuprizone administration (cup+que).

To study the effect of quetiapine on the remyelination process, an additional two groups (6-8 animals/group) of mice were treated with 0.2% cuprizone in milled chow for 6 weeks, and then returned to a cuprizone-free diet (Matsushima and Morell, 2001). Upon resumption of the cuprizone-free diet, mice were fed with either vehicle (water) or quetiapine (10 mg/kg/day in water, que) for 2 weeks.

Behavioral Testing

Locomotor Activity Test

One day before the end of these experiments, spontaneous motor activity was measured using a locomotion detection system equipped with photo-beams. Mice were individually placed in a transparent cage (40×40×25 cm) for 6 minutes, after 1 min adaptation, the frequency of photo-beam interruptions by the mouse in the following 5 min was recorded as the number of total movements (horizontal and vertical) (Bushnell et al., 1986).

Y-maze Spontaneous Alternation

Immediately after the locomotor activity test, spatial working memory was assessed by recording spontaneous alternation behavior in a Y-maze comprised of three 30-cm compartments marked as A, B, and C arms. Spontaneous alternation behavior is based on the natural tendency of rodents to explore a novel environment. In a Y-maze, mice tend to explore the maze by systematically entering each arm. For efficient alternation, mice are required to know which arms have already been visited. Therefore, alternation behavior can be regarded as a measure involving spatial working memory. A mouse with an impaired working memory cannot remember which arm it has just visited, and thus shows decreased spontaneous alternation (Wietrzych et al., 2005). Each mouse was placed at the end of one arm and allowed to move freely through the maze during an 8-min period. The total number and series of arm entries were recorded visually. The number of overlapping entrance sequences (e.g., ABC, BCA) was defined as the number of alternations. The effect was calculated as the percentage of alternation according to the following formula: Percent alternation=(number of alternations)/(total number of arm entries-2)×100 (Wall et al., 2002). Total entries were scored as an index of ambulatory activity in the Y-maze, and mice showing scores below six entries would be excluded.

Tissue Preparation and Immunohistochemical Analysis

At the end of their treatment period, mice were anaesthetized with pentobarbital sodium at 50 mg/kg and perfused intracardially with 0.01 M PBS followed by 4% paraformaldehyde in PBS, and the brains were post-fixated overnight in 4% paraformaldehyde. Brain tissues were then rinsed 3 times with 0.01 M PBS and cryoprotected in 30% sucrose at 4° C. for one day and frozen at −80° C. for immunostaining. Serial coronal sections were dissected between levels 1 to −1 mm bregma, as defined in the mouse brain atlas of Franklin and Paxinos (Franklin and Paxinos, 1997). Demyelination was evaluated in frozen sections (30 μm) of the corpus callosum using Luxol fast blue with periodic acid-Schiff reaction. Floating frozen sections (30 μm) were incubated with 0.3% of $H_2O_2$ in 0.01 M PBS for 30 min at room temperature (RT) for quenching endogenous peroxidase activity, then blocked with 10% goat serum/PBS or 10% rabbit serum (for MBP staining) for 1 hour at RT, and then incubated overnight with the primary antibody(s) diluted in the blocking solution. After rinsing, the sections were incubated with the appropriate biotin-conjugated secondary antibody (1:1000; Vector Laboratories, Burlingame, Calif.) for 1 hour at RT. Sections were then developed with the avidin biotin complex kit (Vector Laboratories, Burlingame, Calif.) and the antibodies were visualized with DAB chromogen (Sigma-Aldrich, St. Louis, Mo.).

Antibodies

A goat polyclonal antibody directed against MBP (1:250; Santa Cruz Biotechnology, CA) was used to detect myelin. A rabbit anti-pi isoform of glutathione S-transferase (GST-pi, 1:500; Stressgen, Victoria, BC, Canada) was used as a marker for mature oligodendrocytes (Mason et al., 2004); Ness et al., 2005). The rabbit polyclonal NG2 antibody (1:200; Chemicon, Temecula, Calif.) was used as a marker for oligodendrocyte progenitors (Nishiyama et al., 1996).

Image Analysis

For GST-pi and NG2 quantification, three digital pictures from the coronal section from each animal (including the middle line and the two edges of the corpus callosum in each section) were examined. Cell counts are expressed as the mean number of positive cells counted in three coronal sections from two different areas, 500 μm apart, between 1 to −1 mm bregma, following the mouse brain atlas of Franklin and Paxinos (Franklin and Paxinos, 1997). Results are expressed as the average of at least 6 mice per group. For MBP staining analysis, three digital pictures from the coronal section (including cerebral cortex) of each animal were examined, at least 6 animals of each group. The percentage of MBP-positive area was calculated in a selected area (FIG. 2.G). Results are expressed as the ratio of average percentage of MBP-positive area compared to control (FIG. 2.H). Images were performed on an Olympus BX-51 light microscope with digital CCD capture system (Diagnostic Instruments Inc., Sterling Heights, Mich.) and analyzed using Image-Pro Plus software (version 4.1, Media Cybernetics, Inc., Silver Spring, Md.).

Statistical Analysis

The results were expressed as means±SEM. A probability of $P<0.05$ was considered to be statistically significant. Statistical significance was determined by analysis of variance (ANOVA), followed by multiple comparisons among treatment groups made with Tukey's test (*$P<0.05$; $P<0.01$; *$P<0.001$). A two-tailed paired Student's t test was used for comparing individual treatment with the control (*$P<0.05$, **$P<0.01$).

Results

Example 1

Cuprizone Markedly Impaired Spontaneous Alternation Behavior that can be Reversed by Co-administration with Quetiapine In the present study, it was found that 0.2% cuprizone administration for 5 weeks markedly impaired spontaneous alternation behavior in the Y-maze and increased the total number of entries in Y-maze arms. Co-administration of quetiapine (10 mg/kg/day, p.o.) significantly attenuated the impairment of spontaneous alternation behavior and decreased the rise of the total number of arm entries induced by cuprizone (FIG. 1. Tukey's test, **$p<0.01$ vs. control, ++$p<0.01$ vs. cuprizone). Memory impairment still remained after 2 weeks of recovery from cuprizone demyelination. Quetiapine treatment during remyelination did not appear to improve memory impairment or alter the total arm entries in the Y-maze (FIG. 1, two-tailed Student's t test, *$p<0.05$, **$p<0.01$). Locomotor activity testing showed no significant difference among groups (data not shown).

Example 2

Co-administration of Quetiapine Reduced Cuprizone-Induced Demyelination

To assess the effect of quetiapine on cuprizone-induced demyelination, mice were fed with 0.2% cuprizone with or without quetiapine co-administration for 5 weeks. Brain sections were then stained by MBP immunostaining for myelin protein and LFB-PAS histology for myelin lipid. Sections from the 5-week cuprizone treatment group showed a significant demyelination in MBP staining; in contrast, sections from the group co-administrated with quetiapine and cuprizone showed less demyelination (35% reduction) (FIG. 2.A-D). LFB-PAS staining showed the same trend as MBP staining (FIG. 3.A-D). After a 2-week recovery from cuprizone demyelination, both MBP and LFB-PAS showed obvious remyelination in demyelinated lesions, but there was no difference between the vehicle (water) and quetiapine treatment on remyelination (FIGS. 2.E, F and 3.E, F).

Example 3

Quetiapine Alters Progenitor Proliferation in Response to Demyelination

In response to demyelination and the depletion of mature oligodendrocytes, NG2+ oligodendrocyte progenitor cells rapidly accumulated within the demyelinating corpus callosum and differentiated into star-like morphology (FIG. 4.E) (Morell et al., 1998; Arnett et al., 2001); whereas, quetiapine co-administration dramatically decreased the number of NG2+ cells within the demyelinated areas (FIG. 4.A-D). While not wishing to be limited by theory, this result suggests that the reduction of demyelination could inhibit the accumulation of NG2+ cells. NG2+ cells were dramatically decreased after 2 weeks recovery from cuprizone treatment. Quetiapine had little effect on this change (FIG. 4.F, G).

Example 4

Quetiapine Treatment Accelerated the Repopulation of Mature Oligodendrocytes During Remyelination After 5 weeks of treatment, cuprizone induced a remarkable loss of mature oligodendrocytes in the corpus callosum, which is partly due to apoptosis (Mason et al., 2000, Arnett et al., 2002). To examine oligodendrocial loss, GST-pi, a mature myelinating oligodendrocyte marker, was stained. In both the cuprizone and cup+que groups, GST-pi+ cells almost totally vanished in the corpus callosum, which indicated that quetiapine did not reverse the loss of mature oligodendrocytes (FIG. 5.A-D). Remyelination occurs when cuprizone is withdrawn from the diet and results in new mature oligodendrocytes present in the demyelinated lesions (Mason et al., 2000). In an in vitro study on neural progenitor cell cultures, quetiapine promoted the proliferation and differentiation of oligodendrocytes. To study if quetiapine treatment could also promote oligodendrocyte remyelination from demyelinated lesions, the GST-pi+ cells in the corpus callosum of mice that recovered from demyelination for 2 weeks were examined. The GST-pi+mature oligodendrocytes were dramatically increased in the quetiapine-treated mice (FIG. 5.E-F)

Discussion

Feeding cuprizone for 5 weeks to young adult mice induces a reproductive and obvious demyelination. When cuprizone is removed, an extensive remyelination takes place within a few weeks (Blakemore et al., 1973). Compared to experimental autoimmune encephalomyelitis (EAE), an inflammatory demyelination model, the cuprizone model has a simpler immunological response with the absence of T cells (Bakker et al., 1987; Hiremath et al., 1998). Therefore, the cuprizone model is thought to be an ideal model for studying de- and re-myelination processes with less immunity response involved.

Based on this model, it was found that quetiapine treatment significantly ameliorates cuprizone-induced demyelination in mouse brain, either by LFB-PAS staining (Pappas et al., 1981) or MBP immunostaining (FIGS. 2 and 3). As a response to demyelination, OPCs accumulate and display star-like morphology in demyelinated lesions (Mason et al., 2000). In the present study, the accumulation of OPCs was also decreased in the cup+que group, accompanied by the reduction of demyelination (FIG. 4). This result demonstrates that alleviating demyelination also inhibits the accumulation of OPCs. While not wishing to be limited by theory, the difference in demyelination might be due to a delay in the loss of myelin-producing oligodendrocytes in quetiapine-treated mice, but GST-pi+ mature oligodendrocytes were almost absent in mice with either cuprizone treatment or co-administrated with quetiapine (FIG. 5). It seems that demyelination and the loss of mature oligodendrocytes are not coincident at this time point, as previously addressed by McMahon and colleagues (McMahon et al., 2001). A possible explanation is that although a large number of GST-pi+ mature oligodendrocytes are lost through apoptosis during demyelination (Mason et al., 2000), a few mature oligodendrocytes may still survive with down-regulation of the GST-pi gene (Tansey et al., 1997) and, therefore, cannot be detected by GST-pi staining, which contributes to the absence of GST-pi cells (McMahon et al., 2001).

Again, while not wishing to be limited by theory, it is assumed that feeding cuprizone results in a decreased activity of cytochrome oxidase and a disturbance of energy metabolism in the mitochondria (Suzuki et al., 1969; Wakabayashi et al., 1978); that it decreases the activities of SOD (Ljutakova et al., 1985) and monoamine oxidase (Kesterson et al., 1971) and, thereby, induces oligodendrocyte apoptosis and demyelination. Recent studies have addressed inflammatory cytokines such as interferons (Mana et al., 2006; Lin et al., 2006, Gao et al., 2000) and tumor necrosis factor-α (TNF-α) (Arnett et al., 2001; McMahon et al., 2001), and growth factors like PDGF (Murtie et al., 2005; Woodruff et al., 2004), FGF2

(Armstrong et al., 2002) and IGF-1 (Mason et al., 2000; Mason et al., 2003) that are also involved in the de- and re-myelination processes. Other studies reported that quetiapine and other APDs were able to suppress apoptosis (He et al., 2004; Luo et al., 2004; Jarskog et al., 2006), protect cells against oxidative stress (Wang et al., 2005) and NMDA medicated excitotoxic injury (Farber et al., 1993; Farber et al., 1996), and up-regulate neural growth factor expression (e.g., NGF, GDNF, BDNF) (Xu et al., 2002; Parikh et al., 2003). Thus, it is hypothesized that these aspects of APDs (including quetiapine) may contribute to the protection of myelin from demyelination.

Studies show that about 40-60% of MS patients suffer cognitive impairment (Penman et al., 1991; McIntosh-Michaelis et al., 1991; Rao et al., 1991), including memory, attention, conceptualization and problem-solving skills, and information processing (Petersen et al., 1989). Among these, memory deficits, especially the long-term memory and working memory, are most typically involved (Grant et al., 1984; Beatty et al., 1988). In the cuprizone model, it was found that the decline of working memory impairment, displayed in the Y-maze test, was reversed by quetiapine treatment (FIG. 1). Animal studies have also shown that quetiapine could reverse memory deficits induced by phencyclidine (He et al., 2006) and kainic acid (Martin et al., 2005).

As a first report about memory impairment in a cuprizone model, it is hypothesized that memory impairment is associated with demyelination lesions and, thereby, the cuprizone model may be applied as an MS model, not only for demyelination studies, but also for evaluating demyelination-related memory deficits. When the challenge of cuprizone is terminated, remyelination occurs spontaneously.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Full Citations for Documents Referred to in the Specification

Altschuler E L and Kast R E. 2005. The atypical antipsychotic agents ziprasidone (correction of zisprasidone), risperidone and olanzapine as treatment for and prophylaxis against progressive multifocal leukoencephalopathy. Med Hypotheses. 65(3):585-586.

Andrews H E, Nichols P P, Bates D, Turnbull D M. 2005. Mitochondrial dysfunction plays a key role in progressive axonal loss in multiple sclerosis. Med Hypotheses 64 (4): 669-677.

Armstrong R C, Le T Q, Frost E E, Borke R C, Vana A C. 2002. Absence of fibroblast growth factor 2 promotes oligodendroglial repopulation of demyelinated white matter. J Neurosci. (19):8574-8585.

Arnett H A, Hellendall R P, Matsushima G K, Suzuki K. Laubach V E, Sherman P, Ting J R 2002. The protective role of nitric oxide in a neurotoxicant-induced demyelinating model. J Immunol. 168(1):427-433.

Arnett H A, Mason J, Marino M, Suzuki K, Matsushima G K, Ting J P. 2001. TNF alpha promotes proliferation of oligodendrocyte progenitors and remyelination. Nat. Neurosci. (11):1116-1122.

Bai O, Wei Z L., Lu W, Bowen R, Keegan D, Li X-M. 2002. Protective effects of atypical antipsychotic drugs on PC12 cells after serum withdrawal. J Neurosci Res. 69(2): 278-283.

Bakker D A and Ludwin S K. 1987. Blood-brain barrier permeability during cuprizone-induced demyelination. Implications for the pathogenesis of immune-mediated demyelinating diseases. J Neurol Sci 78(2):125-137.

Barkhatova V P, Zavalishin I A, Askarova L Sh, Shavratskii V Kh, Demina E G. 1998. Changes in neurotransmitters in multiple sclerosis. Neurosci Behav Physiol 28 (4):341-344.

Baum S, Ashok A, Gee G, Dimitrova S, Querbes W, Jordan J, Atwood W J. 2003. Early events in the life cycle of JC virus as potential therapeutic targets for the treatment of progressive multifocal leukoencephalopathy. J Neurovirol. 9 (Suppl) 1:32-37.

Beatty W W, Goodkin D E, Monson N, Beatty P A, Hertsgaard D. 1988. Anterograde and retrograde memory amnesia in patients with chronic-progressive multiple sclerosis. Arch Neurol. 45(6):611-619.

Blakemore W F. 1973. Remyelination of the superior cerebella peduncle in the mouse following demyelination induced by feeding cuprizone. J Neurol Sci 20(1):73-83.

Bosboom J L and Wolters E C. 2004. Psychotic symptoms in Parkinson's disease: pathophysiology and management. Expert Opin Drug Saf. 3(3):209-220. Review.

Brown (2004) U.S. Patent Application Publication No. 20040058910, Mar. 25, 2004.

Bushnell P J. 1986. Differential effects of amphetamine and related compounds on locomotor activity and metabolic rate in mice. Pharmacol Biochem Behav. 25(1):161-170.

Carson S, McDonagh M S, Peterson K. 2006. A systematic review of the efficacy and safety of atypical antipsychotics in patients with psychological and behavioral symptoms of dementia. J Am Geriatr Soc. 54(2):354-361.

Chang A, Tourtellotte W W, Rudick R, Trapp B D. 2002. Premyelinating oligodendrocytes in chronic lesions of multiple sclerosis. N Engl J Med. 346 (3):165-173.

Farber N B, Foster J, Duhan N L, Olney J W. 1996. Olanzapine and fluperlapine mimic clozapine in preventing MK-801 neurotoxicity. Schizophr Res 21(1):33-37.

Farber N B, Price M T, Labruyere J, Nemnich J, St Peter H, Wozniak D F, Olney J W. 1993. Antipsychotic drugs block phencyclidine receptor-mediated neurotoxicity. Biol Psychiatry 34(1-2):119-121.

Franklin K B J and Paxinos G. 1997. The mouse brain in stereotaxic coordinates. San Diego: Academic Press.

Fujimura M, Hashimoto K, Yamagami K. 2000. Effects of antipsychotic drugs on neurotoxicity, expression of fos-like protein and c-fos mRNA in the retrosplenial cortex after administration of dizocilpine. Eur J Pharmacol. 398 (1):1-10.

Gao K, Gajwani P, Elhaj O, Calabrese J R. 2005. Typical and atypical antipsychotics in bipolar depression. J Clin Psychiatry. 66(11):1376-1385.

Gao X, Gillig T A, Ye P, D'Ercole A J, Matsushima G K, Popko B. 2000. Interferon-gamma protects against cuprizone-induced demyelination. Mol Cell Neurosci. 16(4): 338-349.

Gilgun-Sherki Y, Melamed E, Offen D. 2004. The role of oxidative stress in the pathogenesis of multiple sclerosis: the need for effective antioxidant therapy. J Neurol. 251(3):261-268.

Goldstein, J. (2004) U.S. Patent Application Publication No. 20040058909.

Grant I, McDonald W I, Trimble M R, Smith E, Reed R. 1984. Deficient learning and memory in early and middle phases of multiple sclerosis. J Neurol Neurosurg Psychiatry. 47(3):250-255.

Hashimoto K, Fujimura M, Yamagami K. 2000. Dizocilpine-induced neuropathological changes in rat retrosplenial cortex are reversed by subsequent clozapine treatment. Life Sci. 66 (12):1071-1078.

He J, Xu H, Yang Y, Rajakumar D, Li X, Li X-M. 2006. The effects of chronic administration of quetiapine on the phencyclidine-induced reference memory impairment and decrease of Bcl-XL/Bax ratio in the posterior cingulate cortex in rats. Behav Brain Res. 168(2):236-242.

He J, Xu H, Yang Y, Zhang X, Li X-M. 2004. Neuroprotective effects of olanzapine on methamphetamine-induced neurotoxicity are associated with an inhibition of hyperthermia and prevention of Bcl-2 decrease in rats. Brain Res. 1018(2):186-192.

He J, Xu H, Yang Y, Zhang X, Li X-M. 2005. Chronic administration of quetiapine alleviates the anxiety-like behavioural changes induced by a neurotoxic regimen of dl-amphetamine in rats. Behav Brain Res. 160(1):178-187.

Hiremath M M, Saito Y, Knapp G W, Ting J P, Suzuki K, Matsushima G K. 1998. Microglial/macrophage accumulation during cuprizone-induced demyelination in C57BL/6 mice. J Neuroimmunol. 92(1-2):38-49.

Jarskog L F, Gilmore J H, Glantz L A, Gable K L, German T T, Tong R I, Lieberman J A. 2006. Caspase-3 Activation in Rat Frontal Cortex Following Treatment with Typical and Atypical Antipsychotics. Neuropsychopharmacology. 2006 Apr. 12. Epub ahead of print.

Kesterson J W and Carlton W W. 1971. Monoamine oxidase inhibition and the activity of other oxidative enzymes in the brains of mice fed cuprizone. Toxicol Appl Pharmacol. 20(3):386-395.

Lassmann H. 2005. Multiple sclerosis pathology: evolution of pathogenetic concepts. Brain Pathol. 2005 July; 15(3): 217-222.

Lin W, Kemper A, Dupree J L, Harding H P, Ron D, Popko B. 2006. Interferon-gamma inhibits central nervous system remyelination through a process modulated by endoplasmic reticulum stress. Brain. 129(Pt 5):1306-1318.

Ljutakova S G and Russanov E M. 1985. Differences in the in vivo effects of cuprizone on superoxide dismutase activity in rat liver cytosol and mitochondrial intermembrane space. Acta Physiol Pharmacol Bulg. 11(2):56-61.

Lovas G, Szilagyi N, Majtenyi K, Palkovits M, Komoly S. 2000. Axonal changes in chronic demyelinated cervical spinal cord plaques. Brain. 123 (Pt 2):308-317.

Luo C, Xu H, Li X-M. 2004. Post-stress changes in BDNF and Bcl-2 immunoreactivities in hippocampal neurons: effect of chronic administration of olanzapine. Brain Res. 1025(1-2):194-202.

Mana P, Linares D, Fordham S, Staykova M, Willenborg D. 2006. Deleterious Role of IFN{gamma} in a Toxic Model of Central Nervous System Demyelination. Am J Pathol. 168(5):1464-1473.

Martin M V, Dong H, Bertchume A, Csernansky J G. 2005. Low dose quetiapine reverses deficits in contextual and cued fear conditioning in rats with excitotoxin-induced hippocampal neuropathy. Pharmacol Biochem Behav. 82(2):263-269.

Mason J L, Jones J J, Taniike M, Morell P, Suzuki K, Matsushima G K. 2000b. Mature oligodendrocyte apoptosis precedes IGF-1 production and oligodendrocyte progenitor accumulation and differentiation during demyelination/remyelination. J Neurosci Res. 61(3):251-262.

Mason J L, Toews A, Hostettler J D, Morell P, Suzuki K, Goldman J E, Matsushima G K. 2004. Oligodendrocytes and progenitors become progressively depleted within chronically demyelinated lesions. Am J Pathol 64(5):1673-1682.

Mason J L, Xuan S, Dragatsis I, Efstratiadis A, Goldman J E. 2003. Insulin-like growth factor (IGF) signaling through type 1 IGF receptor plays an important role in remyelination. J Neurosci. 23(20): 7710-7718.

Mason J L, Ye P, Suzuki K, D'Ercole A J, Matsushima G K. 2000a. Insulin-like growth factor-1 inhibits mature oligodendrocyte apoptosis during primary demyelination. J Neurosci. 20(15):5703-5708.

Matsushima G K and Morell P. 2001. The neurotoxicant, cuprizone, as a model to study demyelination and remyelination in the central nervous system. Brain Pathol. 11(1): 107-116.

McIntosh-Michaelis S A, Wilkinson S M, Diamond I D, McLellan D L, Martin J P, Spackman A J. 1991. The prevalence of cognitive impairment in a community survey of multiple sclerosis. Br J Clin Psychol 30:333-348.

McMahon E J, Cook D N, Suzuki K, Matsushima G K. 2001. Absence of macrophage-inflammatory protein-1alpha delays central nervous system demyelination in the presence of an intact blood-brain barrier. J Immunol. 167(5): 2964-2971.

Morell P, Barrett C V, Mason J L, Toews A D, Hostettler J D, Knapp G W, Matsushima G K. 1998. Gene expression in brain during cuprizone-induced demyelination and remyelination. Mol Cell Neurosci. 12(4-5):220-227.

Murtie J C, Zhou Y X, Le T Q, Vana A C, Armstrong R C. 2005. PDGF and FGF2 pathways regulate distinct oligodendrocyte lineage responses in experimental demyelination with spontaneous remyelination. Neurobiol Dis. 19(1-2):171-182.

Ness J K, Valentino M, McIver S R, Goldberg M P. 2005. Identification of oligodendrocytes in experimental disease models. Glia. 50(4):321-328.

Nishiyama A, Lin X-H, Giese N, Heldin C-H, Stallcup W B. 1996. Co-localization of NG2 proteoglycan and PDGFα-receptor on O2A progenitor cells in the developing rat brain. J Neurosci Res 43(3):299-314.

Pappas C. 1981. CNS myelin and synapses in a spontaneous mouse ovarian teratoma showing neural differentiation. An immunohistochemical and electron microscopic study. J Neuropathol Exp Neurol. 40(3):289-297.

Parikh V, Evans D R, Khan M, Mahadik S P. 2003. Nerve growth factor in never-medicated first-episode psychotic and medicated chronic schizophrenic patients: possible implications for treatment outcome. Schizophrenia Res. 60(2-3):117-123.

Penman M F. 1991. Assessing the prevalence of cognitive impairment in multiple sclerosis: implications for patient management. Axone 13 (2): 45-49.

Petersen R C and Kokmen E. 1989. Cognitive and psychiatric abnormalities in multiple sclerosis. Mayo Clinic Proceedings. 64 (6): 657-663.

Pitt D, Werner P, Raine C S. 2000. Glutamate excitotoxicity in a model of multiple sclerosis. Nat. Med. (1):67-70.

Prineas J W, Barnard R O, Kwon E E, Sharer L R, Cho E S. 1993. Multiple sclerosis: remyelination of nascent lesions. Ann Neurol. 33(2):137-151.

Qing H, Xu H, Wei Z, Gibson K D, Li X-M. 2003. The ability of atypical antipsychotic drugs vs. haloperidol to protect PC12 cells against MPP+-induced apoptosis. Eur J Neurosci 17 (8):1563-1570.

Raine C S and Wu E. 1993. Multiple sclerosis: remyelination in acute lesions. J Neuropathol Exp Neurol. 52(3):199-204.

Rao S M, Leo G J, Bernardin L, Unverzagt F. 1991. Cognitive dysfunction in multiple sclerosis. I. Frequency, patterns and prediction. Neurology 1991; 41(5):685-691.

Smith K J, Kapoor R, Felts P A. 1999. Demyelination: the role of reactive oxygen and nitrogen species. Brain Pathol. 9 (1), 69-92.

Stover J F, Pleines U E, Morganti-Kossmann M C, Kossmann T, Lowitzsch K, Kempski O S. 1997. Neurotransmitters in cerebrospinal fluid reflect pathological activity. Eur J Clin Invest 27 (12):1038-1043.

Suzuki K and Kikkawa T. 1969. Status spongiosus of CNS and hepatic changes induced by cuprizone (bis-cyclohexanone oxalyldihydrazone). Am J Pathol 54(2):307-325.

Tansey, F A, Zhang H, Cammer W. 1997. Rapid upregulation of the Pi isoform of glutathione-S-transferase in mouse brains after withdrawal of the neurotoxicant, cuprizone. Mol. Chem. Neuropathol. 31(2):161-170.

Thanvi B R, Lo T C, Harsh D P. 2004. Atypical antipsychotics in the treatment of affective symptoms: a review. Ann Clin Psychiatry. 16(1):3-13. Review.

Wakabayashi T, Asano M, Ishikawa K, Kishimoto H. 1978. Mechanism of the formation of megamitochondria by copper-chelating agents. V. Further studies on isolated megamitochondria. Acta Pathol Jpn. 28(2):215-223.

Wall P M and Messier C. 2002. Infralimbic kappa opioid and muscarinic M1 receptor interactions in the concurrent modulation of anxiety and memory. Psychopharmacology (Berl). 160(3):233-244.

Wang H, Xu H, Dyck L E, Li X-M. 2005. Olanzapine and quetiapine protect PC12 cells from beta-amyloid peptide (25-35)-induced oxidative stress and the ensuing apoptosis. J Neurosci Res. 81(4):572-580.

Wei Z, Bai O, Richardson J S, Mousseau DD, Li X-M. 2003. Olanzapine protects PC12 cells from oxidative stress induced by hydrogen peroxide. J Neurosci Res. 73(3):364-368.

Wietrzych M, Meziane H, Sutter A, Ghyselinck N, Chapman P F, Chambon P, Krezel W. 2005. Working memory deficits in retinoid X receptor gamma-deficient mice. Learn Mem. 12(3):318-326.

Wolswijk G. 1998. Chronic stage multiple sclerosis lesions contain a relatively quiescent population of oligodendrocyte precursor cells. J Neurosci. 18 (2):601-609.

Woodruff R H, Fruttiger M, Richardson W D, Franklin R J. 2004. Platelet-derived growth factor regulates oligodendrocyte progenitor numbers in adult CNS and their response following CNS demyelination. Mol Cell Neurosci. 25(2):252-262.

Xu H, Qing H, Lu W, Keegan D, Richardson J S, Chlan-Fourney J, Li X-M. 2002. Quetiapine attenuates the immobilization stress-induced decrease of brain-derived neurotrophic factor expression in rat hippocampus. Neurosci Lett. 321(1-2): 65-68.

Zamvil, S S and Steinman L. 2003. Diverse targets for intervention during inflammatory and neurodegenerative phases of multiple sclerosis. Neuron 38(5):685-688.

What is claimed is:

1. A method of treating multiple sclerosis comprising administering to a subject in need thereof, an effective amount of a compound selected from quetiapine and analogs of quetiapine, and pharmaceutically acceptable salts, solvates and prodrugs thereof, wherein the quetiapine, or analogs of quetiapine, attenuates the demyelination of nerve cells and promotes repopulation of mature oligodendrocytes.

2. The method according to claim 1 wherein the compound is administered long term.

3. The method according to claim 1, wherein the compound is quetiapine or a pharmaceutically acceptable salt thereof.

4. The method according to claim 3, wherein the compound is quetiapine hemi-fumarate.

5. The method according to claim 1, wherein the analogs of Quetiapine are selected from a compound of Formula I, and pharmaceutically acceptable salts, solvates and prodrugs thereof:

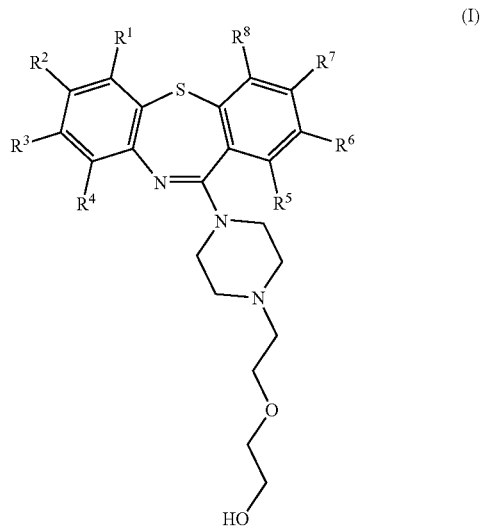

(I)

wherein one to four of $R^1$, $R^2$, $R^3$, $R^4$, $R^5$, $R^6$, $R^7$ and $R^8$ are independently selected from Br, Cl, I, F, OH, $OCH_3$, $CF_3$, $OCF_3$ $CH_3$, $CH_2CH_3$, $CH_2CH_2CH_3$, $CH_2(CH_3)_2$, $CH_2CH_2CH_2CH_3$, $CH_2CH_2(CH_3)_2$ and $C(CH_3)_3$.

* * * * *